United States Patent [19]

Shartzer

[11] 4,427,226

[45] Jan. 24, 1984

[54] PLASTIC LENS INSERTION AND REMOVAL DEVICE

[76] Inventor: Ewart E. Shartzer, 1150 Riverside Dr., Akron, Ohio 44310

[21] Appl. No.: 370,728

[22] Filed: Apr. 22, 1982

[51] Int. Cl.³ .............................................. A61F 9/06
[52] U.S. Cl. ................................................ 294/1 CA
[58] Field of Search ............. 294/1 CA, 16, 33, 99 R; 51/216 LP, 217 L; 81/43; 128/303 R, 321; 206/5.1; 351/160

[56] References Cited

U.S. PATENT DOCUMENTS 3,910,618 10/1975 Massenz ............................ 294/1 CA
4,190,277 2/1980 England ............................. 294/1 CA
4,192,204 3/1980 Feldman ............................ 294/1 CA

*Primary Examiner*—James B. Marbert
*Attorney, Agent, or Firm*—Oldham, Oldham, Hudak, Weber & Sand Co.

[57] ABSTRACT

Apparatus to position or remove a plastic lens including an eyelid opener having upper and lower crossbars for individual engagement with the person's upper and lower eyelids to retain them open, and plastic lens engaging tweezer having a pair of resilient arms with a flexible lens engaging member thereon for engaging the plastic lens in the wearer's eye and removing the same.

8 Claims, 7 Drawing Figures

PLASTIC LENS INSERTION AND REMOVAL DEVICE

TECHNICAL FIELD

The invention herein lies in the art of plastic lens and apparatus for position or to remove the plastic lens from a wearer's eye.

BACKGROUND ART

In the past decade, plastic lenses have been becoming more and more used by all members of the public. These plastic lenses are soft and need to be inserted into the person's eye daily and naturally be removed from the eye once or more per day. Many people have some appreciable difficulty in the insertion and/or removal of these plastic lenses and one of the problems committing to difficulties in plastic lens insertion and removal is retention of the person's eyelids open for positioning or removal of the plastic lens.

Heretofore a number of different plastic lens applicators have been proposed and a variety of these members including a resilient cup for engaging the wearer's eye includes the structure shown in U.S. Pat. No. 3,910,618 while contact lens applicator is shown in U.S. Pat. No. 3,129,971. Yet other structures for manipulating contact lenses and involving some type of a flexible eye cup member include the structure shown in U.S. Pat. Nos. 2,379,629 and 3,139,298. However, none of such prior apparatus, insofar as I am aware, make it really easy for the average person to hold his eyelids open and then readily insert the contact lens or remove the same as desired.

DISCLOSURE OF INVENTION

The general object of the present invention is to provide a novel and improved plastic lens removal and/or insertion device which is readily usable by the average person and which greatly facilitates control and use of plastic lenses.

Another object of the invention is to provide an easily controlled eyelid opener unit which a person can carefully but readily engage with his upper and lower eyelids to retain the eyelids open by the unit engaged with one hand, and then to have a tweezer unit controlled by the other hand readily engageable with the person's eye and lens thereon for contact lens removal or replacement as desired.

Another object of the invention is to provide an improved unit, controlled by one hand, so as to be able to readily squeeze an end of the unit into engagement with the contact lens to remove it from a wearer's eye, or to position the contact lens in the eye and then release it from engagement with the tweezer unit and have it operatively positioned in the eye.

Other objects of the invention are to provide an easily transportable contact lens control apparatus including a carrier case for receiving a small apparatus for facilitating contact lens control action.

Yet another object of the invention is to provide a mechanical device which is not expensive and which is easily controlled by the average person to facilitate an improved contact lens controlled by the person.

The foregoing and other objects and advantages of the invention will be made more apparent as the specification proceeds, are achieved by: apparatus for positioning or removing a plastic lens into or from a person's eye comprising: the combination of an eyelid opener including upper and lower cross-bars adapted to be individually engaged with a person's upper and lower eyelids respectively and retain them open; and a plastic lens engaging tweezer that has a pair of arms with a flexible lens engaging means extending between the free ends of the tweezer arms and controlled by the arms for engaging or releasing the plastic lens.

Additionally, apparatus for positioning or removing a contact or plastic lens into or from a person's eye comprising: the combination of an eyelid opener including upper and lower crossbars on a control handle and adapted to be individually engaged with a person's upper and lower eyelids respectively and retain them open; and a plastic lens engaging tweezer that has a pair of resilient arms with a flexible lens engaging means extending between the free ends of the tweezer arms whereby said lens engaging means can be engaged with a plastic lens in a wearer's eye; the arms be squeezed together slightly and the plastic lens be engaged and removed from the wearer's eye.

BRIEF DESCRIPTION OF DRAWINGS

Reference now is particularly directed to the accompanying drawings, wherein.

When referring to corresponding members shown in the drawings and referred to in the specification, corresponding numerals are used to facilitate comparison therebetween.

BEST MODE FOR CARRYING OUT THE INVENTION

Figure 1:
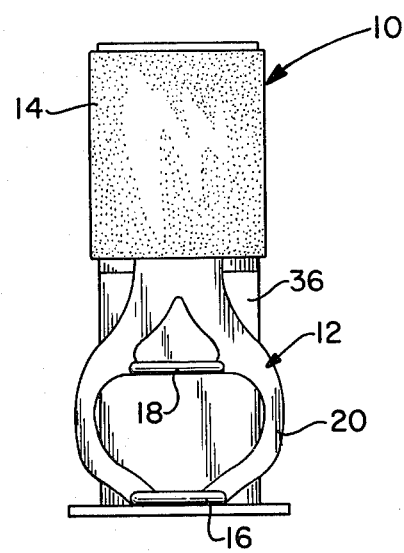
FIG. 1 is an elevation of the contact lens control apparatus of the invention as inoperatively positioned in the carrier unit.
Figure 2:
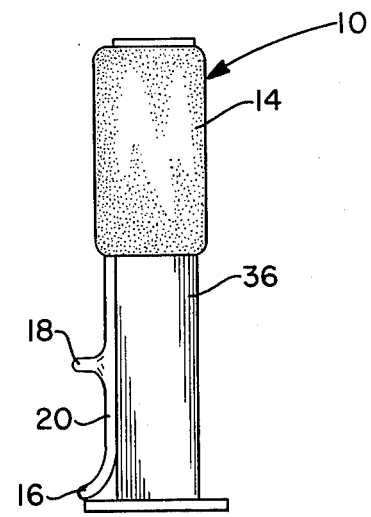
FIG. 2 is a right side elevation of the apparatus of FIG. 1.
Figures 3, 4:
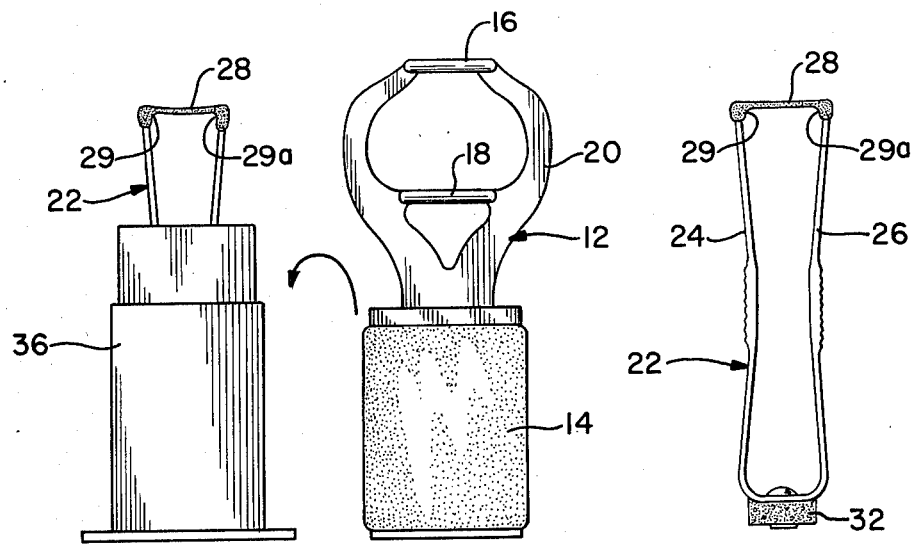
FIG. 3 is an elevation view like FIG. 1 but with the top portion of the carrier case removed and positioned in upright position.
FIG. 4 is a plan view of a contact lens engaging tweezer of the invention.

This invention relates to apparatus for positioning or removing a plastic lens into or from a person's eye which apparatus comprises the combination of an eyelid opener including upper and lower crossbar means on a carrier member and adapted to have the crossbars individually engaged with a person's upper and lower eyelids and retain them open; and a plastic lens engaging tweezer with a pair of resilient arms having a flexible lens engaging means carried by and extending between the free ends of the tweezer arms whereby this lens engaging means can be engaged with a plastic lens in a wearer's eye by squeezing the arms together slightly to engage the lens and facilitate its removal from the wearer's eye after which the eyelid opener is released from engagement with the person's eyelids and the plastic lens is removed; and wherein insertion of the plastic lens occurs by a substantial reversal of the actions described.

Attention now is particularly directed to the details of the structure in the accompanying drawings, and the apparatus of the invention for positioning or removing a plastic lens into or from a person'eye is indicated as whole by the numeral 10 and it, in general, comprises an eyelid opener member 12 which includes a handle section 14 and upper and lower crossbars 16 and 18 operatively secured to this handle 14 as by a frame section 20. This upper frame section and upper and lower crossbars 16 and 18, together with the handle 14, are made from any suitable type of material such as a plastic that can be readily molded and which will be easy to maintain clean over a good service life. The upper and lower crossbars are curved at center sections thereof so as to be substantially complementary in shape to a person's eyeball and to be offset from a more or less vertical plane defined by the remainder of the frame 20 that operatively positions these upper and lower crossbars in kind of offset relationship to the frame section 20 and its relationship to the handle 14.

Figure 6:
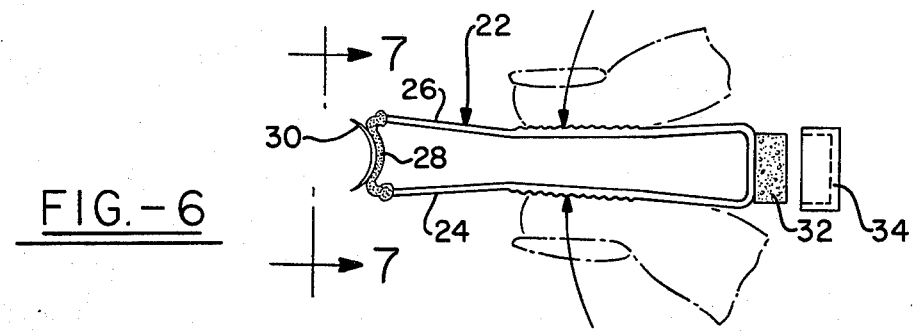
FIG. 6 is a top plan of the contact lens tweezer article of the invention.
Figure 7:
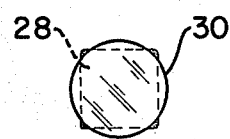
FIG. 7 is a front elevation taken on line 7—7 of the contact lens tweezer unit of FIG. 6.

A second important portion of the apparatus of the invention comprises a plastic or contact lens engaging tweezer 22 that includes a pair of flexibly associated arms 24 and 26 that operatively position a flexible contact lens engaging means 28. This contact engaging lens means member or cup usually is formed from molded resilient material such as natural or synthetic rubber and it may have end portions that can be telescoped into engagement with the arms 24 and 26 or be otherwise suitably secured thereto. The portion of this cup or means 28 between the arms 24 and 26 is more or less strap-like and will readily retain a concave shape or be compressed into a more severe concave shape than is shown in FIG. 6. Thus the edges or kind of end portions of this means 28 can be slightly thicker or be reinforced in the opposed inner parts of this means 28, as indicated at 29, 29a so that the member will retain its concave shape and flex inwardly readily.

Figure 5:
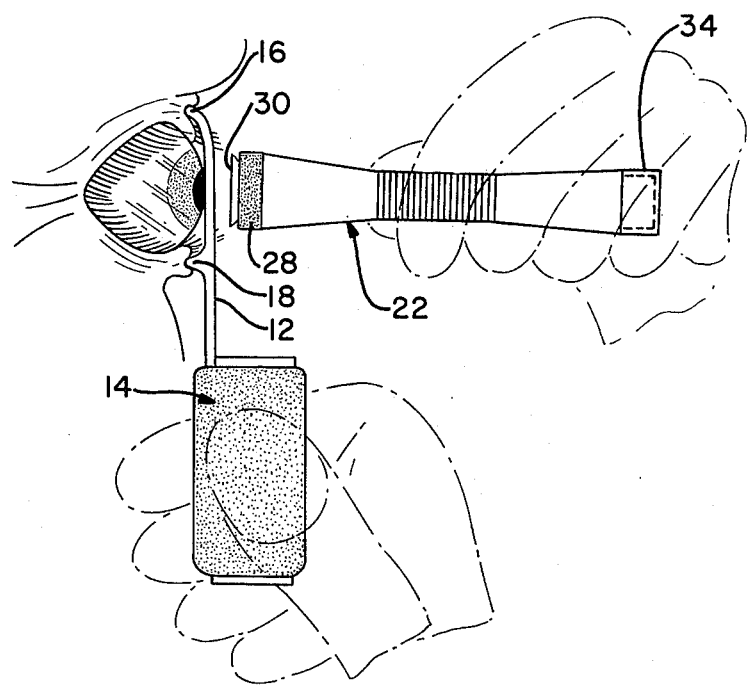
FIG. 5 is an elevation indicating engagement of the eyelid opener operatively engaging a person's eye and with the tweezer unit carrying a contact lens approaching the eye.

It should be noted that FIG. 5 indicates how the apparatus of the invention preferably is used and wherein the user would manipulate the eyelid opener 21 so that upper crossbar 16 and particularly the center section thereof would be engaged with the person's upper eyelid and then the eyelid opener, which would have been pointed towards the upper eyelid, would then be swung downwardly through a short arc to bring the center portion of the lower crossbar into engagement with the wearer's lower eyelid, as indicated in solid lines in FIG. 5. This action then positively holds the person's eyelid open with this opener 12 being controlled by one hand of the wearer and then the person by his other hand engages the tweezer 22 so as to insert or remove a contact lens 30 from association with the person's eye.

The spacing apart of the free ends of this tweezer 22 and the shape of the length of the cup 28 is such as to enable the wearer to bring the cup 28 into engagement with the contact lens 30 and squeeze the arms together slightly to engage the contact lens by the tweezer and enable it to be removed from contact with the wearer's eyeball. Naturally if one is positioning the contact lens 30 in the wearer's eye, then the tweezer arms 24 and 26 would pick up the contact lens from its carrier case or other position and bring the contact lens up into association with the eyeball at which time the arms 24 and 26 would be released slightly while the lens is pressed up against the eyeball so as to deposit the contact lens on the wearer's eyeball.

It should be noted that the baase portion of the tweezer 22 is shown with a small sponge 32 thereon and suitably secured thereto. This sponge may have a little cup or cap 34 of any conventional type positioned removably thereover whereby the sponge 32 can have a suitable saline solution or sanitary liquid received therein. Thus, the contact lens 30 can be touched to this sponge 32 when the cap 34 is removed to provide a little lubricant thereon or the sponge can be touched to the lens when it is operatively positioned. The sponge 32 normally has a concave surface and the lens may be placed on the sponge for application to the wearer's eyeball. Any other suitable retention compartment for a lubricant solution can be provided and the sponge 32 may be dipped therein prior to any lubricating action, as desired.

It will be seen that the handle 14 can be made into more or less the shape of a cup-like member that would telescope over a base 36 provided for the eyelid opener 12 so as to be able to position or telescope the eyelid opening into this base 36. The base 36 would receive the tweezer unit 22 therein and provide a convenient carrier case for the apparatus of the invention.

From the foregoing, it should be realized that relatively easily controlled and inexpensive but effectively operating and easily used contact lens positioning apparatus has been provided by the invention. The wearer can use both hands to position his plastic lens but readily control his eyelids to retain them open while easily engaging a contact lens to position it in the eyeball or remove it therefrom as desired. Thus the objects of the invention have been achieved.

While one complete embodiment of the invention has been disclosed herein, it will be appreciated that modification of this particular embodiment of the invention may be resorted to without departing from the scope of the invention.

What is claimed is:

1. Apparatus for positioning or removing a plastic lens into or from a person's eye comprising:
   the combination of an eyelid opener including a handle and upper and lower crossbars adapted to be individually engaged with a persons's upper and lower eyelids respectively and retain them open; and
   a plastic lens engaging tweezer that has a pair of arms with a flexible lens engaging means extending between the free ends of the tweezer arms and controlled by the arms for engaging or releasing the plastic lens, said handle being positioned by one hand below the persons eye, and said tweezer being positioned and controlled by the persons other hand and being substantially horizontal to extend between said cross bars to position a plastic lens on the persons eyeball.

2. Apparatus as in claim 1, where said crossbars are curved to be complementary to the shape of an eyeball and are offset from a planar vertically positioned part of the eyelid opener, when operatively positioned to facilitate engaging such crossbars with a person's eyelids.

3. Apparatus for positioning or removing a contact or plastic lens into or from a persons's eye comprising:
   the combination of an eyelid opener including upper and lower crossbars on a control handle and adapted to be individually engaged with a person's upper and lower eyelids respectively and retain them open, said crossbars having side frame means connecting them and an open center area; and a plastic lens engaging tweezer that has a pair of resilient arms with a flexible lens engaging means extending between the free ends of the tweezer arms whereby said lens engaging means can be inserted through said open center area and be engaged with a plastic lens in a wearer's eye; the arms being squeezed together slightly and the plastic lens be engaged and removed from the wearer's eye.

4. Apparatus as in claim 3, where said crossbars are curved to be complementary to the shape of an eyeball and said crossbars are substantially parallel and are positioned offset from the handle to facilitate engaging such crossbars with a person's eyelids, and said lens engaging means has a cup-like end.

5. Apparatus as in claims 3 or 4, where said control handle includes a box-like section, and a box member is provided and is adapted to engage said box-like section, said tweezer being positionable in said box member.

6. Apparatus as in claim 1, where said lens engaging means may be as wide or wider than a plastic lens or contract lens and it includes a deformable cup-like section for engaging the lens.

7. Apparatus as in claim 1, where said tweezer arms normally are in spaced substantially parallel relation and where said flexible lens engaging means includes a strap-like concave faced lens engaging section readily controlled in shape and/or in operative length by squeezing said tweezer arms together.

8. Apparatus as in claim 3, where said tweezer arms normally are in spaced substantially parallel relation and where said flexible lens engaging means includes a strap-like concave faced lens engaging section readily controlled in shape and/or in operative length by squeezing said tweezer arms together to aid in engaging and releasing a plastic lens.

* * * * *